United States Patent [19]

Harbert

[11] 4,013,662
[45] Mar. 22, 1977

[54] ALKYL AND BENZYL 6,7-DIALKOXY-2-METHYL-4-OXO-1,2,3,4-TETRAHYDROQUINOLINE-1-CARBOXYLATES

[75] Inventor: Charles A. Harbert, Waterford, Conn.

[73] Assignee: Pfizer Inc., New York, N.Y.

[22] Filed: Nov. 4, 1975

[21] Appl. No.: 628,809

Related U.S. Application Data

[63] Continuation-in-part of Ser. No. 534,659, Dec. 19, 1974, abandoned, which is a continuation-in-part of Ser. No. 428,441, Dec. 26, 1973, abandoned.

[52] U.S. Cl. .................. 260/287 K; 260/468 K; 260/471 A; 260/475 R; 260/578; 424/258
[51] Int. Cl.² ................................. C07D 215/22
[58] Field of Search .............. 260/287 K, 287

[56] References Cited

UNITED STATES PATENTS

| | | | |
|---|---|---|---|
| 2,421,693 | 6/1947 | Harriman | 260/287 |
| 3,347,856 | 10/1967 | Lunsford | 260/287 |
| 3,446,805 | 5/1969 | Wirth et al. | 260/287 K |
| 3,455,929 | 7/1969 | Belleau et al. | 260/287 |
| 3,637,846 | 1/1972 | Plostnieks | 260/287 K |

FOREIGN PATENTS OR APPLICATIONS 229,393  7/1960  Australia ..................... 260/287

OTHER PUBLICATIONS

Bekhli, "Chemical Abstracts," 1970, vol. 72, p. 327, Abst. 121,309c.

*Primary Examiner*—Donald G. Daus
*Assistant Examiner*—David E. Wheeler
*Attorney, Agent, or Firm*—Connolly and Hutz

[57] ABSTRACT

The racemic mixture, and the dextrorotatory enantiomer, of a compound of the formula

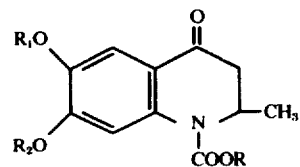

wherein R is alkyl having from one to four carbon atoms or benzyl, and $R_1$ and $R_2$ are each alkyl having from one to four carbon atoms, are useful as analgesic and tranquilizing agents in mammals.

8 Claims, No Drawings

ALKYL AND BENZYL 6,7-DIALKOXY-2-METHYL-4-OXO-1,2,3,4-TETRAHYDROQUINOLINE-1-CARBOXYLATES

CROSS-REFERENCE TO RELATED APPLICATIONS

This application is a continuation-in-part of application Ser. No. 534,659, filed Dec. 19, 1974, and now abandoned which is a continuation of application Ser. No. 428,441, filed Dec. 26, 1973, and now abandoned.

BACKGROUND OF THE INVENTION

This invention relates to novel alkyl and benzyl 6,7-dialkoxy-2-methyl-4-oxotetrahydroquinoline-1-carboxylates which have useful therapeutic properties in the field of medicinal chemistry. More particularly, the compounds of the present invention are useful as analgesic and tranquilizer agents.

SUMMARY OF THE INVENTION

This invention relates to novel chemical compounds and to their use as analgesic and tranquilizing agents. In particular the invention relates to the racemic mixture, and the dextrorotatory enantiomer, of a compound of the formula

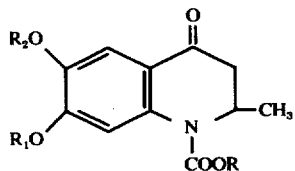

where R is selected from the group consisting of alkyl having from one to four carbon atoms and benzyl, and $R_1$ and $R_2$ are each alkyl having from one to four carbon atoms. Particularly effective compounds of the invention are the racemic mixture and the dextrorotatory enantiomer of ethyl 6,7-dimethoxy-2-methyl-4-oxo-1,2,3,4-tetrahydroquinoline-1-carboxylate and benzyl 6,7-dimethoxy-2-methyl-4-oxo-1,2,3,4-tetrahydroquinoline-1-carboxylate.

DETAILED DESCRIPTION OF THE INVENTION

The compounds of this invention have the formula

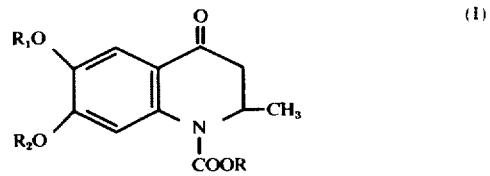

wherein R, $R_1$ and $R_2$ are as previously defined. As will be recognized by one with skill in the art, the compounds represented by the formula I possess as asymmetric carbon atom, and therefore they can exist in two forms. These forms can be distinguished by their ability to rotate the plane of plane-polarized light. One form rotates the plane of polarized light to the right and is known as the dextrorotatory enantiomer or the d-enantiomer; the other form rotates the plane of polarized light to the left and is known as the levorotatory enantiomer or the l-enantiomer. A mixture of equal amounts of the d- and l-enantiomers of a compound of formula I does not affect the plane of plane-polarized light, and it is known as a racemic mixture of dl-form. For the purposes of the present invention, when determining whether a compound is dextrorotatory or levorotatory, it is the effect of the compound on light having a wavelength of 5893 Angstroms (the so-called D line of sodium) which is to be considered.

In the present invention, both the racemic mixtures and dextrorotatory enantiomers of the compounds of the formula I show analgesic and tranquilizing activity; the levorotatory enantiomers of the compounds of formula I do not show analgesic or tranquilizing activity.

In one method according to the invention, a racemic mixture of a compound of the formula I can be prepared in accordance with the following reaction scheme:

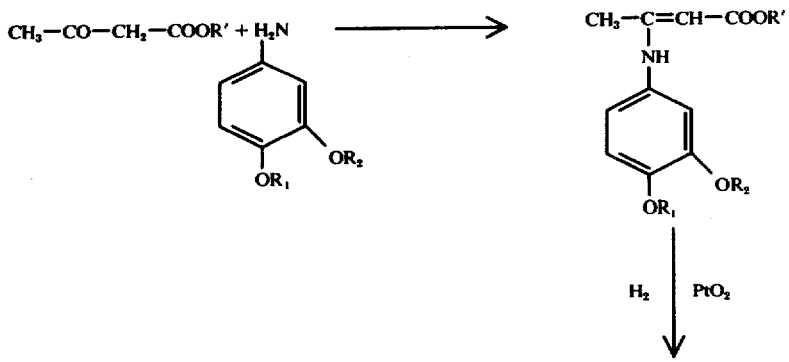

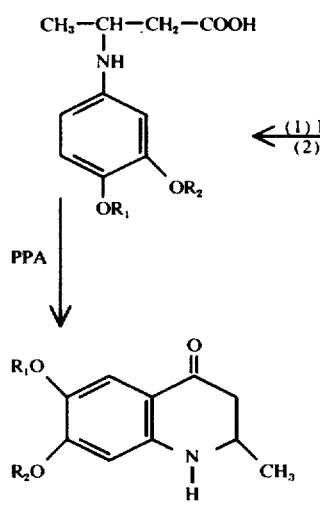

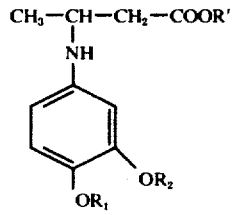

-continued

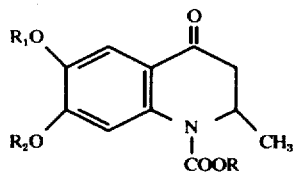

wherein R' is lower-alkyl, and PPA represents polyphosphoric acid.

In the first of the above-depicted reaction steps, an alkyl acetoacetate such as ethyl acetoacetate is condensed with the appropriate 3,4-dialkoxyaniline in the presence of a suitable solvent such as benzene and a small amount of an acid catalyst such as acetic acid. Recovery of the resulting alkyl 3-[(3,4-dialkoxy)anilino]-2-butenoate upon reaction completion, which may be determined by thin layer chromatography, is possible by solvent removal at reduced pressure. Recrystallization from solvents such as hexane yields the desired butenoate intermediate.

The second step of the aforesaid reaction sequence involves hydrogenation of the butenoate product of the first step utilizing conditions for the reduction of double bonds (M. Freifelder, "Practical Catalytic Hydrogenation, Techniques and Applications": Wiley-Interscience, New York, 1971), preferably catalytic hydrogenation over palladium, palladium on carbon or platinum oxide under acidic conditions, i.e., at a pH of about 3 up to 7. Acetic acid is a preferred acid for obtaining this pH. The resulting alkyl 3-[(3,4-dialkoxy)anilino]butanoate may be recovered by filtration of the hydrogenated mixture, concentration under reduced pressure, dissolving resulting product in a solvent such as chloroform, washing with sodium bicarbonate solution and saturated sodium chloride, drying the organic layer using magnesium sulfate and concentration under reduced pressure.

The third step of the process involves alkaline hydrolysis of the product of the second step, employing aqueous sodium or potassium hydroxide together with a water-miscible solvent such as methanol. The resulting 3-[(3,4-dialkoxy)anilino]butanoic acid containing reaction mixture may then be cooled, concentrated under reduced pressure, diluted with water, neutralized with acid and extracted with an agent such as chloroform. The combined organic extracts are then dried, for example using anhydrous magnesium sulfate, and concentrated under reduced pressure to give a product suitable for use in the next step of the process without further purification.

The product of the third reaction step is then cyclized by heating in the presence of excess polyphosphoric acid, which not only serves as the agent responsible for causing cyclization but also serves as solvent for the reaction, or by other Friedel-Crafts type catalysts and non-aqueous solvents as suggested by G. A. Olah, "Friedel Crafts and Related Reactions", Vol. I Interscience Publishers, New York, 1963. The resulting 6,7-dialkoxy-2-methyl-4-oxo-1,2,3,4-tetrahydroquinoline reaction containing mixture may then be poured into ice, extracted with chloroform and recovered by concentrating the combined dried organic extracts under reduced pressure.

The product of the fourth reaction step may then be acylated with an alkyl or benzyl chloroformate in conventional fashion. The desired alkyl or benzyl 6,7-dialkoxy-2-methyl-4-oxo-1,2,3,4-tetrahydroquinoline-1-carboxylate is then recovered from the reaction mixture via extraction, drying of the combined extract layers and concentration under reduced pressure.

If desired, variation in the above-described synthetic scheme can be employed. Thus, it is not essential to hydrolyse the alkyl 3-[(3,4-dialkoxy)anilino]butanoate produced in the second step before proceeding to the cyclization step. The 3-[(3,4-dialkoxy)anilino]butanoates can be cyclized directly to 6,7-dialkoxy-2-methyl-4-oxo-1,2,3,4-tetrahydroquinolines using the same conditions described for the cyclization of the 3-[(3,4-dialkoxy)-anilino]butanoic acids.

In another method according to the invention, a racemic mixture of a compound of formula I can be prepared in accordance with the following reaction scheme:

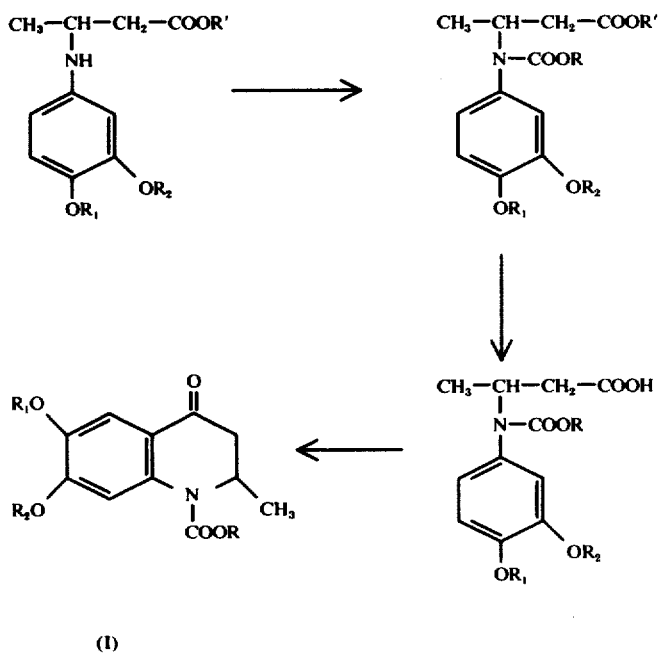

(I)

The above-depicted reaction scheme is shown starting from the appropriate alkyl 3-[(3,4-dialkoxy)anilino]butanoate, preparation of which has already been described. In the first step of the above-depicted scheme, the alkyl 3[(3,4-dialkoxy)anilino]butanoate is acylated with the requisite alkyl or benzyl chloroformate. The reaction is carried out by the method described earlier for the acylation of a 6,7-dialkoxy-2-methyl-4-oxo-1,2,3,4-tetrahydroquinoline.

In the second step of the above-depicted reaction scheme, the alkyl 3-[(3,4-dialkoxy-N-alkoxycarbonyl)anilino]butanoate or 3-[(3,4-dialkoxy-N-benzyloxycarbonyl)anilino]butanoate is selectively hydrolysed to the corresponding 3-[(3,4-dialkoxy-N-alkoxycarbonyl)anilino]butanoic acid or 3-[(3,4-dialkoxy-N-benzyloxycarbonyl)anilino]butanoic acid. This selective hydrolysis can be carried out using either basic or acidic conditions. When it is carried out under acidic conditions, a convenient mode of operation comprises digesting the butanoate ester with hydrochloric acid of concentration from about 2N to about 8N, at a temperature from about 40° C. to about 100° C., for a few hours, e.g., about two hours. When it is carried out under basic conditions, the selective hydrolysis is conveniently effected by treating the ester with one molar equivalent of an alkali metal or alkaline earth metal hydroxide in an aqueous alkanol, such as aqueous methanol or aqueous ethanol, at about ambient temperature. The reaction takes several hours, e.g. overnight, to each completion.

In the third step of the above-depicted reaction scheme, the 3-[(3,4-dialkoxy-N-ethoxycarbonyl)anilino]butanoic or 3-[(3,4-dialkoxy -N-benzyloxycarbonyl)anilino]butanoic acid is cyclized to the corresponding 1,2,3,4-tetrahydroquinoline of formula I.

This cyclization is carried out in the same manner as described earlier for the cyclization of a 3-[(3,4-dialkoxy)anilino]butanoic acid.

If desired, the alkyl 3-[(3,4-dialkoxy-N-alkoxycarbonyl)anilino]-butanoate or 3-[(3,4-dialkoxy-N-benzyloxycarbonyl)anilino]butanoate can be cyclized directly to a racemic compound of formula I, using the same conditions described earlier for the cyclization of a 3-[(3,4-dialkoxy)anilino]-butanoic acid.

The necessary 3,4-dialkoxyaniline starting materials of the present invention are either well known and commercially available, or readily produced by conventional fashion, e.g. in the same manner that 4-aminoveratrole is produced.

The compounds of formula I can be obtained as the d- and l-enantiomers by a variety of methods. For example, one of the previously described procedures for the preparation of a racemic compound of the formula I can be used, with the modification that one of the intermediates is resolved into its optical isomers prior to cyclization. Such a resolution can be carried out, for example, via salt formation with an optically active reagent. Thus, for example, a 3-[(3,4-dialkoxy)anilino]butanoic acid, a 3-[(3,4-dialkoxy-N-alkoxycarbonyl)-anilino]butanoic acid or a 3-[(3,4-dialkoxy-N-benzyloxycarbonyl)anilino]-butanoic acid can be resolved by salt formation with an optically active amine, followed by fractional recrystallization, according to standard procedures. Other methods of resolution can be visualized readily by one with skill in the art.

However, a particularly convenient method of obtaining the d- and l-isomers of a compound of formula I, involves preparation of a racemic compound of the formula I, followed by separation according to the following scheme:

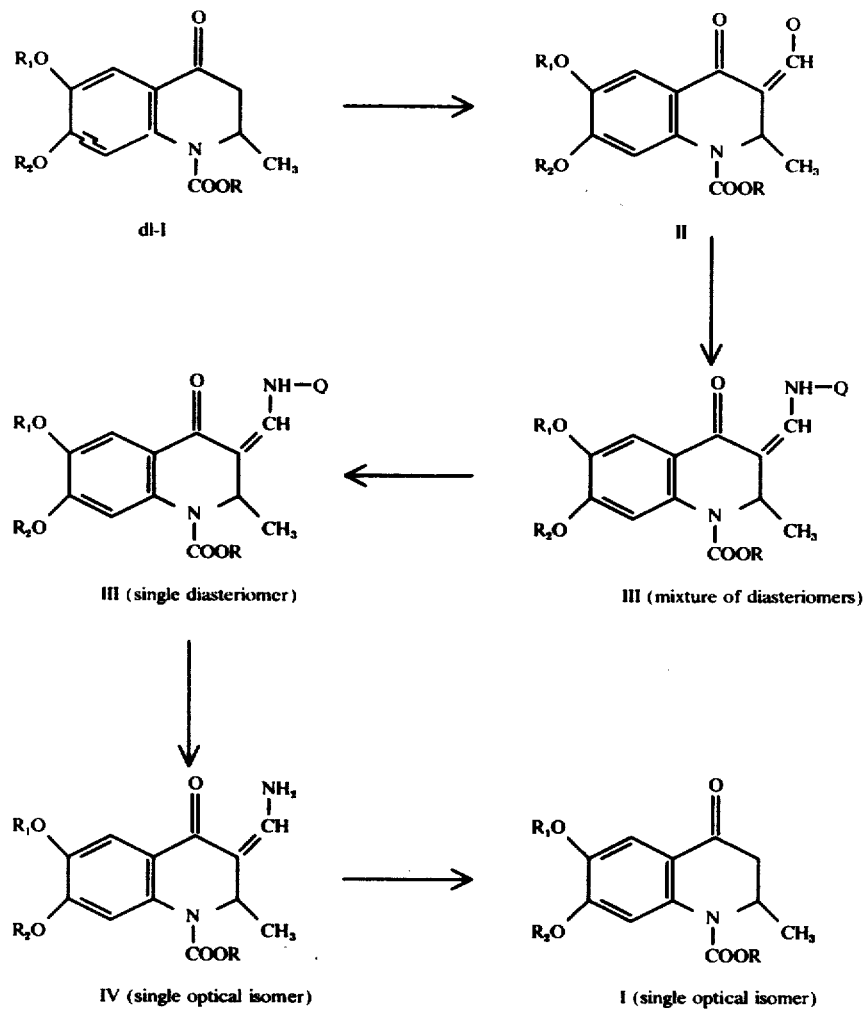

In the first step of the above-depicted reaction scheme, the racemic compound of formula I is condensed with ethyl formate, in the presence of a strong base, to give the 3-hydroxymethylene derivative of formula II. The condensation can be carried by methods well-known in the art, and a convenient procedure involves treating the racemic compound of formula I with an excess of ethyl formate, in the presence of at least one molar equivalent of sodium ethoxide in a reaction-inert organic solvent, at about ambient temperature, for a few hours. The product can be recovered by treatment of the reaction medium with water, acidification and extraction into a water-immiscible organic solvent. Removal of the solvent by evaporation affords the required hydroxymethylene compound.

In the second step of the above-depicted scheme, the hydroxymethylene compound of formula II is reacted with one of the optical isomers of an amine of the formula $NH_2Q$ which as an asymmetric center in the group Q. This reaction produces a compound of the formula III, as a mixture of two diastereomers. These diastereomers are then separated in conventional fashion, e.g. by fractional crystallization or by chromatography. A wide variety of amines of the formula $NH_2Q$ can be used, and one skilled in the art will realize that a particular amine will be chosen so that it affords the widest possible difference in physical properties, i.e. solubility and-/or polarity, in the two diastereomers of the formula III. For the purposes of the present invention, 1-(1-naphthyl)ethylamine is a particularly convenient amine. The reaction of the hydroxymethylene compound of the formula II with the amine of the formula $NH_2Q$ is usually carried out by contacting equimolar amounts of the two reagents in a reaction-inert organic solvent such as benzene, at about ambient temperature, for several hours, e.g. overnight. Removal of the solvent by evaporation then affords the product.

After separation into the single diastereomers, each diastereomer of the formula III is then treated with ammonium acetate. This reaction, which is normally conducted using a large excess of ammonium acetate in a refluxing solvent such as ethanol, for several hours, brings about an amine exchange, and procedures the compounds of the formula IV in the d- and the l-form.

The d and l-enantiomers of the compounds of the formula IV can then be converted into the d- and l-enantiomers of a compound of the formula I, by alkaline hydrolysis. The compound of formula IV is treated with one molar equivalent of an alkali or alkaline earth metal hydroxide, such as sodium or potassium hydroxide, in the presence of a co-solvent such as ethanol or methanol. The reaction takes about 24 hours, and then the crude product is then isolated by solvent evaporation.

In some instances, the crude product from the hydrolysis of the aminomethylene compound of the formula IV is contaminated with the corresponding 6,7-dialkoxy-2-methyl-4-oxo-1,2,3,4-tetrahydroquinoline, i.e. the product in which the alkoxy- or benzyloxycarbonyl group has been removed from the nitrogen atom of the tetrahydroquinoline. When this occurs to a significant extent, it is convenient to treat the reaction product with the appropriate chloroformate of formula Cl-CO-OR, in the presence of a base, thereby increasing the ultimate yield of the optically active compound of formula I.

Acid-catalysed hydrolysis of a compound of the formula IV also leads to the corresponding compound of the formula I. However, at least under certain conditions, acid-catalysed hydrolysis of an optically-active compound of the formula IV is accompanied by racemization.

The compounds of the present invention are conveniently administered in composition form. Such compositions include a pharmaceutical carrier selected on the basic of the chosen route of administration and standard pharmaceutical practice. For example, they may be administered orally in the form of tablets containing such excipients as starch, milk, sugar, certain types of clays, etc. or they may be administered in capsules in admixture with the same or equivalent excipients. They may also be administered orally in the form of oral suspensions which may contain flavoring and coloring agents. Furthermore, they may be injected parenterally, i.e., for example, intramuscularly or subcutaneously. For oral administration, tablets or capsules containing from about 25 to about 500 mg. are suitable for most applications.

The physician will determine the dosage which will be most suitable for an individual patient and this dosage will vary with the form of administration, the age, weight and response of the particular patient. Generally, however, adult dosage will range from 25 to 1500 mg. per day divided into two to four equal doses. In many instances, it will not be necessary to exceed 600 mg. daily.

The following examples are for the purpose of illustrating the present invention and the temperatures reported therein are in degrees Centigrade unless otherwise specified.

EXAMPLE 1

Ethyl 3-[(3,4-Dimethoxy)anilino]-2-butenoate

4-Aminoveratole (62.0 g.), ethyl acetoacetate (63.0 g.), benzene (375 ml), and acetic acid (2.1 ml) were combined and refluxed in a flask equipped with a Dean-Stark trap to remove water until thin layer chromatography indicated the reaction was complete. The solvent was removed under reduced pressure to give a dark oil which crystallized upon standing. Recrystallization from hexane gave 79.0 g of a tan powder, m.p. 59°–60°; a second crop afforded 6.7 g, m.p. 54°–56°. A sample was recrystallized from ethanol/water to give an analytical sample, m.p. 57°–58°.

Analysis: Calcd. for $C_{14}H_{19}NO_4$: C, 63.38; H, 7.22; N, 5.28;

Found: C, 63.45; H, 7.06; N, 5.33.

EXAMPLE 2

Ethyl 3 ([3,4-Dimethoxy)anilino butanoate

A mixture of 30.0 g of the product of Example 1 (m.p. 59°–60°), and 2.0 g of platinum oxide in 250 ml of acetic acid was hydrogenated in a Paar shaker at 50 p.s.i.; reduction was complete in 1 hr. The mixture was filtered and concentrated under reduced pressure, to give an amber oil which was dissolved chlorofrm and washed with sodium bicarbonate solution followed by saturated sodium chloride. The organic layer was dried over magnesium sulfate and concentrated under reduced pressure to give 30.0 g of an amber oil which was used in the next step without further purification. A sample of oil was converted to the hydrochloride salt, m.p. 137.5°–139°. An equivalent sample of the hydrochloride salt (m.p. 138°–139.5°) was analyzed.

Analysis: Calcd. for $C_{14}H_{21}NO_4 \cdot HCl$: C, 55.35; H, 7.30; N, 4.61;

Found: C, 55.73; H, 7.33; N, 4.33.

EXAMPLE 3

3-[(3,4-Dimethoxy)anilino]butanoic Acid

A 54-g sample of the unpurified ester product of Example 2 was combined with 17.5 g of sodium hydroxide, 550 ml of methanol and 130 ml of water, and refluxed for 1.5 hrs. The reaction mixture was cooled, concentrated under reduced pressure, diluted with water and neutralized with 6N hydrochloric acid to give an oily mixture which was extracted with chloroform. The combined organic extracts were dried over anhydrous magnesium sulfate and concentrated under reduced pressure to give 48 g of an oily product. This material was used in the next step without further purification.

EXAMPLE 4

6,7-Dimethoxy-2-methyl-4-oxo-1,2,3,4-tetrahydroquinoline

The crude acid of Example 3 (48 g) and 500 g of polyphosphoric acid were heated for 1 hr. on a steam bath with vigorous stirring, then poured onto 700 g of ice and extracted with chloroform. The organic extracts were dried over anhydrous magnesium sulfate and concentrated under reduced pressure to give 26.4 g of yellow solid, m.p. 145°–48°. A small sample was sublimed at 110° (.05 mm) to give a pale yellow solid, m.p. 150°–151°.

Analysis: Calcd. for $C_{12}H_{15}O_3N$: C, 65.14; H, 6.83; N, 6.33;

Found: C, 65.18; H, 6.86; N, 6.25.

EXAMPLE 5

Racemic Ethyl 6,7-Dimethoxy-2-methyl-4-oxo-1,2,3,4-tetrahydroquinoline-1-carboxylate A mixture of 15 g. of the quinoline product of Example 4, 95 g. of potassium carbonate, and 225 ml. of methylene chloride was stirred for 1 hr., then 14.7 g. of ethyl chloroformate in 20 ml. of methylene chloride was added dropwise and the suspension was allowed to stir for 72 hrs. at room temperature. Additional 7.3 g. portions of ethyl chloroformate were added after 24 and 48 hrs. and 47 g. of potassium carbonate was added after 48 hrs. The reaction mixture was quenched with water and extracted several times with methylene chloride. The combined organic extracts were washed with water, dried over magnesium sulfate and concentrated under reduced pressure to give an oil which solidified upon standing; trituration with 5% ethyl acetate in hexane gave 17 g. of a solid, m.p. 112°–116°. This solid was chromatographed on silica gel, eluting with 1:1 ethyl acetate/hexane, and recrystallized from 1:1 ethyl acetate/hexane to give 13.9 g. of white crystals, m.p. 116.5°–18°.

Analysis: Calcd. for $C_{15}H_{19}NO_5$: C, 61.42; H, 6.53; N, 4.78;

Found: C, 61.37; H, 6.51; N, 4.78.

EXAMPLE 6

Racemic Methyl 6,7-Dimethoxy-2-methyl-4-oxo-1,2,3,4-tetrahydroquinoline-1-carboxylate A mixture of 1.2 g. (5.45 mmol) of the quinoline product of Example 4, 792 mg. (10.7 mmol) of dry pyridine and 5.5 ml. of methylene chloride was stirred and cooled by an ice-water bath while 758 mg. (8.02 mmol) of methyl chloroformate in 1 ml. of methylene chloride was added over a 10 min. period at a rate to maintain a 10°–15° C. temperature. The ice bath was removed and the reaction allowed to stir at room temperature for 45 min. then poured onto 25 ml. of saturated sodium bicarbonate solution. The methylene chloride layer was separated and washed with 25 ml. saturated sodium bicarbonate solution and saturated sodium chloride solution, then dried over magnesium sulfate, and gravity filtered and evaporated to a yellow solid. The solid was triturated with 5 ml. anhydrous ether, filtered, and washed with minimum ether, then air dried to 1.1 g. of a yellow solid, m.p. 156°–158°. This material was dissolved in 10 ml. of hot ethyl acetate, treated with 50 mg. Darco G60, filtered and crystallized by the addition of hexane to give 727 mg. of an off-white solid, m.p. 159°–160° after drying in vacuum at 100° C (1 mm) for 24 hrs.

Analysis: Calculated for $C_{14}H_{17}O_5N$: C, 60.20; H, 6.13; N, 5.01;

Found: C, 60.31; H, 6.30; N, 5.33.

EXAMPLE 7

Racemic Butyl 6,7-Dimethoxy-2-methyl-4-oxo-1,2,3,4-tetrahydroquinoline-1-carboxylate To a cooled mixture of 1.15 g. (5.17 mmol) of the quinoline product of Example 4, 751 mg. (10.15 mmol) of dry pyridine and 5.5 ml. of methylene chloride stirred under a nitrogen atmosphere was added dropwise 1.03 g. (7.60 mmol) of butyl chloroformate in 1 ml. methylene chlroide over 10 min. at a rate to maintain a 10°–15° temperature. After the addition was complete the bath was removed, the reaction stirred at room temperature for 45 min., and poured onto 25 ml. saturated sodium bicarbonate solution. The organic phase was collected and washed with 25 ml. of saturated sodium bicarbonate solution, 50 ml. saturated sodium chloride solution, dried over magnesium sulfate, then gravity filtered and evaporated to a viscous amber oil. Evaporative distillation at 101°C (0.05 mm) gave 1.4 g. of a very viscous amber oil.

Analysis: Calculated for $C_{17}H_{23}O_5N$: C, 63.53; H, 7.21; N, 4.36;

Found: C, 63.73; H, 7.16; N, 4.07.

EXAMPLE 8

Racemic Benzyl 6,7-Dimethoxy-2-methyl-4-oxo-1,2,3,4-tetrahydroquinoline-1-carboxylate To a stirred solution of 10.0 g. (0.45 mol.) of 6,7-dimethoxy-2-methyl-4-oxo-1,2,3,4-tetrahydroquinoline in 76 ml. of pyridine, at 0° C, was added, dropwise, during a 30 minute period, 45 ml. of benzyl chloroformate. Stirring was continued for 15 minutes, and then an additional 10 ml. of benzyl chloroformate was added. After a further 10 minutes, a further 10 ml. of benzyl chloroformate was added. The reaction mixture was heated on a steam bath for 30 minutes, cooled to room temperature and then poured into a mixture of 950 ml. of chloroform and 300 ml. of water. The separated chloroform layer was washed successively with dilute hydrochloric acid, saturated sodium bicarbonate, and water, and then it was dried (MgSO$_4$) and concentrated to dryness in vacuo. The residue was an oil which solidified after trituration with ehtyl acetate-hexane. The resulting solid was then recrystallized from the same solvent system, giving 11.4 g. of the title compound, m.p. 127.5°–129.5° C (71% yield). Further recrystallization of a small portion of the product from ethyl acetate-hexane raised the melting point to 128.5°–130° C.

EXAMPLE 9

Ethyl 3-[(3,4-Dimethoxy-N-ethoxycarbonyl)anilino]butanoate

To a stirred mixture of 1,310 g. of ethyl 3-[(3,4-dimethoxy)anilino]-butanoate, 746 g. of anhydrous potassium carbonate and 5.0 liters of chloroform, under nitrogen, at 5° C., was added dropwise during 10 minutes, 580 g. of ethyl chloroformate. The temperature was maintained below 10° C. during the addition. Stirring was then continued at 3°–8° C. for 15 minutes, at ambient temperature overnight, and then at reflux temperature for 1 hour. To the cooled reaction mixture was added 900 g. of super cel (a diatomaceous earth), and the mixture was then filtered. The filtrate was combined with corresponding filtrates from two identical experiments. This latter solution was washed with water, followed by saturated sodium bicarbonate, followed again by water. The solution was then dried using anhydrous magnesium sulfate, decolorized using activated charcoal, and evaporated in vacuo. This afforded 4,157 g. of the title compound as a viscous oil (yield 83%).

Analysis: -Calcd for $C_{17}H_{25}NO_6$(percent): C, 60.16; H, 7.43; N, 4.13;

Found (percent): C, 60.54; H, 7.66; N, 4.33.

EXAMPLE 10

3-[(3,4-Dimethoxy-N-ethoxycarbonyl)anilino]-butanoic Acid by Acidic Hydrolysis of its Ethyl]Ester A stirred mixture of 1.0 kg. of ethyl 3-[(3,4-dimethoxy-N-ethoxycarbonyl)anilino]butanoate and 10 liters of 6N hydrochloric acid was heated to 80° C. during a 40 minute period, and then maintained at 80°–86° C. for 1.5 hours. The reaction mixture was cooled to 25° C. and the product was extracted into chloroform. The extract was combined with the corresponding extract from an identical experiment. To this chloroform solution was then added 7 liters of water, and the pH was adjusted to 9.4 using sodium hydroxide solution. The layers were separated, and to the aqueous phase was added 3.8 liters of fresh chloroform. The pH was lowered to 2.0 using concentrated hydrochloric acid, and the chloroform layer was removed. It was dried using anhydrous magnesium sulfate and then evaporated in vacuo. This afforded 1755 g. of the title compound as an oil, which solidified on standing. The yield was 96%.

EXAMPLE 11

3-[(3,4-Dimethoxy-N-ethoxycarbonyl)anilino]-butanoic Acid by Basic Hydrolysis of its Ethyl Ester To a stirred solution of 9.5 g. of ethyl 3-[(3,4-dimethoxy-N-ethoxycarbonyl)anilino]butanoate in 28 ml. of ethanol was added 28 ml. of 1N sodium hydroxide. The mixture was stirred at ambient temperature overnight and then the ethanol was removed by evaporation in vacuo. To the residue was added 50 ml. of water and the resulting solution was extracted with ethyl acetate. The extracts were discarded, and the aqueous phase was acidified to pH 2 with 10% hydrochloric acid. The acidified aqueous was extracted with ethyl acetate, and the latter extract was dried and evaporated in vacuo. This afforded 7.0 g. (80% yield) of the title compound as an oil.

Analysis: Calcd. for $C_{15}H_{21}NO_6$(percent): C, 57.86; H, 6.80; N, 4.50; Found (percent): C, 57.95; H, 6.66; N, 4.37.

EXAMPLE 12

Racemic Ethyl 6,7-Dimethoxy-2-methyl-4-oxo-1,2,3,4-tetrahydroquinoline-1-carboxylate To 19 kg. of polyphosphoric acid, pre-heated to 70°–75° C., was added 3.8 kg. of ethyl 3-[(3,4-dimethoxy-N-ethoxycarbonyl)anilino]butanoate in small portions, so as to prevent excess foaming. At the end of the addition, the reaction mixture was maintained at 90°–100° C. for 2 hours. The reaction mixture was then poured into a large excess of ice-water, and the product was extracted into chloroform. The chloroform was dried using anhydrous magnesium sulfate and then concentrated in vacuo to a viscous, red oil. A portion (approximately half) of this latter oil was taken and chromatographed using silica gel as absorbant and eluting with chloroform. The appropriate fractions were combined and evaporated in vacuo, to give 900 g. of the title compound. After recrystallization from ethyl acetate-cyclohexane it weighed 638 g., and it had m.p. 113°–115° C.

Analysis: Calcd. for $C_{15}H_{19}O_5N$ (percent): C, 61.42; H, 6.53; N, 4.78; Found (percent): C, 61.44; H, 6.56; N, 4.83.

EXAMPLE 13

Racemic Ethyl 6,7-Dimethoxy-2-methyl-4-oxo-1,2,3,4-tetrahydroquinoline-1-carboxylate To 7.7 kg. of polyphosphoric acid, preheated to 50° C., was added a mixture of 1,385 g. of 3-[(3,4-dimethoxy-N-ethoxycarbonyl)anilino]butanoic acid and 500 ml. of chloroform, at such a rate that the reaction temperature was maintained at 50°–65° C. without external heating. At the end of the addition, the temperature was maintained at 50°–65° C. for a further 2 hours. The reaction mixture was quenched by adding it slowly to a stirred mixture of 20 liters of ice-water and 8 liters of chloroform, which was then stirred until all the solids had dissolved. The chloroform layer was removed and the aqueous layer was extracted further with chloroform. The combined chloroform layers were washed with saturated sodium bicarbonate, dried using anhydrous magnesium sulfate, and then decolorized with activated carbon. The chloroform was removed by distillation at steam bath temperature, leaving an oil. To the oil was added 2 liters of ethanol followed by 4 liters of hexane. The solid which precipitated was removed by filtration, giving 1020 g. of crude product. The crude product was recrystallized from ethanol, giving 977 g. of racemic ethyl 6,7-dimethoxy-2-methyl-4-oxo-1,2,3,4-tetrahydroquinoline-1-carboxylate, m.p. 115.5°–117° C. (Yield 75%)

EXAMPLE 14

Racemic Ethyl 6,7-Dimethoxy-2-methyl-4-oxo-1,2,3,4-tetrahydroquinoline-1-carboxylate To a stirred solution of 1.17 g. of 3-[(3,4-dimethoxy-N-ethoxycarbonyl)anilino]butanoic acid in 25 ml. of toluene was added 1.5 g. of phosphorus pentoxide, and the resulting suspension was heated at reflux for 1 hour. The hot toluene was then decanted from the dark brown residue. The residue was washed with a further portion of hot toluene, and the combined toluene solutions were then evaporated in vacuo. This afforded 983 mg. of a yellow oil which solidified on the addition of 3 ml. of ethanol. The solid was recovered by filtration, giving 740 mg. (74% yield) of the title compound, m.p. 115°–117° C.

EXAMPLE 15

Condensation of the appropriate 3,4-dialkoxyaniline with ethyl acetoacetate according to the procedure of Example 1, followed by hydrogenation of the product thus obtained according to the procedure of Example 2, produces the following compounds: ethyl 3-[(3,4-diethoxy)anilino]butanoate, ethyl 3-[(3,4-dibutoxy)anilino]butanoate and ethyl 3-[(3-methoxy-4-isopropoxy)anilino]butanoate, respectively.

EXAMPLE 16

Reaction of the butanoate esters of Example 15 with ethyl chloroformate, according to the procedure of Example 9, followed by cyclization with polyphosphoric acid, according to the procedure of Example 12, produces the following compounds in racemic form:
ethyl 6,7-diethoxy-2-methyl-4-oxo-1,2,3,4-tetrahydroquinoline-1-carboxylate,
ethyl 6,7-dibutoxy-2-methyl-4-oxo-1,2,3,4-tetrahydroquinoline-1-carboxylate and
ethyl 6-isopropoxy-7-methoxy-2-methyl-4-oxo-1,2,3,4-tetrahydroquinoline-1-carboxylate, respectively.

EXAMPLE 17

Racemic Ethyl 6,7-Dimethoxy-3-hydroxymethylene-2-methyl-4-oxo-1,2,3,4-tetrahydroquinoline-1-carboxylate To sodium ethoxide, freshly prepared from 4.8 g. of sodium hydride and 6.0 ml. of ethanol was added a solution of 14.7 g. of ethyl 6,7-dimethoxy-2-methyl-4- oxo-1,2,3,4-tetrahydroquinoline-1-carboxylate and 19.8 ml. of ethyl formate in 150 ml. of benzene, over a 45 min. period. The reaction mixture was stirred at room temperature for 3 hrs. and then it was poured onto 250 ml. of ice water. The layers were separated, and the organic layer was extracted with 1N sodium hydroxide solution. The combined aqueous phases were washed with benzene, and then they were added dropwise to 250 ml. of 12N hydrochloric acid. This caused the product to separate in the form of an oil. Recrystallization of this oil from hexane produced 15.4 g. (96% yield) of the title compound, m.p. 98°–101° C. Further recrystallization from hexane raised the melting point to 129°–130° C.

Analysis: Calcd. for $C_{16}H_{19}NO_6$ (percent): C, 59.80; H, 5.96; N, 4.36; Found (percent): C, 59.70; H, 5.90; N, 4.26.

EXAMPLE 18

Reaction of Racemic Ethyl 6,7-Dimethoxy-3-hydroxymethylene-2-methyl-4-oxo-1,2,3,4-tetrahydroquinoline-1-carboxylate with d-1-(1-Naphthyl)ethylamine and Separation of the Diasteriomers A mixture of 6.4 g. of racemic ethyl 6,7-dimethoxy-3-hydroxymethylene-2-methyl-4-oxo-1,2,3,4-tetrahydroquinoline-1-carboxylate and 3.2 g. of d-1-(1-naphthyl)ethylamine in 60 ml. of benzene were stirred at ambient temperature for 16 hours. The solvent was removed by evaporation in vacuo, and the residue was re-dissolved in 250 ml. of chloroform. The chloroform solution was washed with 150 ml. of 1N sodium hydroxide, and then the dried organic phase was concentrated to dryness in vacuo. This afforded 9.3 g. of ethyl 6,7-dimethoxy-3-[N-(1-(1-naphthyl]ethyl)aminomethylene]-2-methyl-4-oxo-1,2,3,4-tetrahydroquinoline-1-carboxylate as a mixture of two diasteriomers, $[\alpha]_D^{25} = -364.17°$ (1% solution in $CHCl_3$).

A 2.0-g. aliquot of the above mixture of diasteriomers was dissolved in 30 ml. of chloroform, and to the resultant solution was added 20 g. of chromatographic grade silica gel. The chloroform was then removed by evaporation in vacuo, and the residue was placed on top of a chromotographic column which had been prepared by placing 760 g. of silica gel in a 50 × 1.6 inch nylon tube. The column was eluted with 1,280 ml. of 15:1 benzene-acetonitrile, and then allowed to run dry. The column was cut into small pieces, approximately 1 inch long, and each piece was triturated with ethyl acetate. The silica gel was removed by filtration, and the ethyl acetate was removed by evaporation in vacuo, giving 15 column fractions.

Fractions 1–5 were combined, giving 290 mg. of the more polar diasteriomer of the above diasteriomeric mixture. This diasteriomer had $[\alpha]_D^{25} = -247.1°$ (1% in $CHCl_3$).

Fractions 14 and 15 were combined, giving 250 mg. of the less polar diasteriomer of the above diasteriomeric mixture. It had $[\alpha]_D^{25} = -407.2°$ (1% in $CHCl_3$).

Fractions 6–13 were rechromatographed, to provide further quantities of each of the pure diasteriomers.

EXAMPLE 19 d-Ethyl 6,7-Dimethoxy-3-aminomethylene-2-methyl-4-oxo-1,2,3,4-tetrahydroquinoline-1-carboxylate To a solution of 2.06 g. of the more polar diasteriomer, prepared by reaction of racemic ethyl 6,7-dimethoxy-3-hydroxymethylene-2-methyl-4-oxo-1,2,3,4-tetrahydroquinoline-1-carboxylate with d-1-(1-naphthyl)ethylamine (see Example 18), in 40 ml. of ethanol, was added 50 g. of ammonium acetate. The reaction mixture was heated to reflux. After 20 minutes reflux and after 45 minutes reflux, additional 25-g. quantities of ammonium acetate were added. The reaction mixture was heated under reflux for a total of 6 hours, and then cooled to 25° C. and poured into 1,000 ml. of ethyl acetate. The ethyl acetate solution was washed successively with water and sodium bicarbonate, dried ($MgSO_4$), and concentrated in vacuo to give 1.55 g. of crude product as a viscous oil. The crude product was purified by column chromatography using silica gel as absorbant and 6:4 benzene-ethyl acetate as eluant, followed by recrystallization from chloroform-hexane, giving 440 mg. of material with melting point of 70°–120° C. A further recrystallization gave 290 mg. of the title compound, m.p. 92–95° C., $[\alpha]_D^{25} = +97.62$ (0.25% in $CHCl_3$).

Analysis: Calc'd. for $C_{16}H_{20}N_2O_5$ (percent): C, 59.99; H, 6.29; N, 8.75; Found (percent): C, 60.08; H, 6.45; N, 8.31.

A further 500 mg. of product having melting point 88°–90° C. was obtained from the recrystallization mother liquors, giving a total yield of 790 mg. (56%).

EXAMPLE 20 d-Ethyl 6,7-Dimethoxy-2-methyl-4-oxo-1,2,3,4-tetrahydroquinoline-1-carboxylate

A mixture of 950 mg. of d-ethyl 6,7-dimethoxy-3-aminomethylene-2-methyl-4-oxo-1,2,3,4-tetrahydroquinoline-1-carboxylate, 2.96 ml. of 1N sodium hydroxide and 4 ml. of ethanol was heated under reflux for 24 hours and then stored at 25° C. for 3 days. The solvent was removed by evaporation in vacuo, and the residue was dissolved in ethyl acetate. The ethyl acetate solution was washed with water and then concentrated to give 970 mg. of an oil. The oil was chromatographed on 40 g. of silica gel, using 6:4 benzene-ethyl acetate as solvent. The early fractions were combined and concentrated in vacuo to give 470 mg. of the title compound as an oil which solidified on standing. This material was recrystallized twice from ethyl acetate-petroleum ether to give 178 mg. (20% yield) of d-ethyl 6,7-dimethoxy-2-methyl-4-oxo-1,2,3,4-tetrahydroquinoline-1-carboxylate, m.p. 94–95° C., $[\alpha]_D^{25} = +135.5$ (0.2% in $CHCl_3$).

Analysis: Calc'd for $C_{15}H_{19}O_5N$(percent): C, 61.42; H, 6.53; N, 4.78,Found(percent): C, 61.46; H, 6.55; N, 4.60.

EXAMPLE 21 l-Ethyl 6,7-Dimethoxy-3-aminomethylene-2-methyl-4-oxo-1,2,3,4-tetrahydroquinoline-1-carboxylate The less polar diasteriomer from the reaction of racemic ethyl 6,7-dimethoxy-3-hydroxymethylene-2-methyl-4-oxo-1,2,3,4-tetrahydroquinoline-1-carboxylate with d-1-(1-naphthyl)ethylamine (see Example 18) was treated with ammonium acetate, according to the procedure of Example 19. This afforded a 46% yield of the title compound, m.p. 92°–95° C., $[\alpha]_D^{25} = -91.52°$ (0.2% in $CHCl_3$).

Analysis:-Calc'd for $C_{16}H_{20}N_2O_5$ (percent): C, 59.99; H, 6.29; N, 8.75; Found (percent): C, 60.37; H, 6.49; N, 8.29.

EXAMPLE 22 l-Ethyl 6,7-Dimethoxy-2-methyl-4-oxo-1,2,3,4-tetrahydroquinoline-1-carboxylate A mixture of 570 mg. of l-ethyl 6,7-dimethoxy-3-aminomethylene-2-methyl-4-oxo-1,2,3,4-tetrahydroquinoline-1-carboxylate, 1.78 ml. of 1N sodium hydroxide and 3 ml. of ethanol was heated under reflux for 24 hours and then stored at 25° C. for 3 days. The solvent was removed by evaporation in vacuo, and the residue was dissolved in ethyl acetate. The ethyl acetate solution was washed with water and then it was concentrated to give 540 mg. of an oil. The oil was chromatographed using 30 g. of silica gel, and using 6:4 benzene-ethyl acetate as solvent, giving 6 fractions. Fractions 1 and 2 were combined and recrystallized from ethyl acetate-hexane to give 49 mg. of the title product, m.p. 92°–93° C. Fractions 3–6 were combined to give 152 mg. of 6,7-dimethoxy-2-methyl-4-oxo-1,2,3,4-tetrahydroquinoline. This latter material was dissolved in 3 ml. of methylene chloride, and 3 ml. of pyridine followed by 0.5 ml. of ethyl chloroformate was added. After 20 minutes, the reaction mixture was diluted with an excess of methylene chloride and water. The organic phase was separated and washed successively with dilute hydrochloric acid, saturated sodium bicarbonate and brine. The methylene chloride solution was then dried, and evaporated in vacuo to give an oil. The oil was recrystallized from ethyl acetate-hexane to give 95 mg. of the title compound, m.p. 92°–93° C.

The two crops of the title compound, together with 45 mg. of equivalent material from an analogous experiment, were further recrystallized to give a sample of the title compound having m.p. 94–95° C., $[\alpha]_D^{25} = -140.7$.

Analysis: Calc'd for $C_{15}H_{19}NO_5$ (percent): C, 61.42; H, 6.53; N, 4.78; Found (percent): C, 61.20; H, 6.38; N, 4.60.

EXAMPLE 23

Condensation of the appropriate, racemic alkyl or benzyl 6,7-dialkoxy-2-methyl-4-oxo-1,2,3,4-tetrahydroquinoline-1-carboxylate with ethyl formate according to the procedure of Example 17, followed by reaction with d-1-(1-naphthyl)ethylamine according to the procedure of Example 18, produces the following compounds, in each case as a mixture of two diasteriomers:

methyl 6,7-dimethoxy-3-[N-(1-[1-naphthyl]ethyl)aminomethylene]-2-methyl-4-oxo-1,2,3,4-tetrahydroquinoline-1-carboxylate, n-butyl 6,7-dimethoxy-3-[N-(1-[1-naphthyl]ethyl)aminomethylene]-2-methyl-4-oxo-1,2,3,4-tetrahydroquinoline-1-carboxylate, benzyl 6,7-dimethoxy-3-[N-(1-[1-naphthyl]ethyl)aminomethylene]-2-methyl-4-oxo-1,2,3,4-tetrahydroquinoline-1-carboxylate, ethyl 6,7-diethoxy-3-[N-(1-[1-naphthyl]ethyl)aminomethylene]-2-methyl-4-oxo-1,2,3,4-tetrahydroquinoline-1-carboxylate, ethyl 6,7-dibutoxy-3-[N-(1-[1-naphthyl]ethyl)aminomethylene]-2-methyl-4-oxo-1,2,3,4-tetrahydroquinoline-1-carboxylate and ethyl 6-isopropoxy-7-methoxy-3-[N-(1-naphthyl)ethyl)aminomethylene]-2-methyl-4-oxo-1,2,3,4-tetrahydroquinoline-1-carboxylate.

Each of the above diasteriomeric mixtures is separated into the individual diasteriomers by chromatography.

EXAMPLE 24

Each of the single diasteriomers obtained after chromatography in Example 23 is treated with ammonium acetate according to the procedure of Example 19, followed by hydrolysis according to the procedure of Example 20, to produce the following compounds in both the dextrorotatory and the levorotatory form:

methyl 6,7-dimethoxy-2-methyl-4-oxo-1,2,3,4-tetrahydroquinoline-1-carboxylate, n-butyl 6,7-dimethoxy-2-methyl-4-oxo-1,2,3,4-tetrahydroquinoline-1-carboxylate, benzyl 6,7-dimethoxy-2-methyl-4-oxo-1,2,3,4-tetrahydroquinoline-1-carboxylate, ethyl 6,7-diethoxy-2-methyl-4-oxo-1,2,3,4-tetrahydroquinoline-1-carboxylate, ethyl 6,7-dibutoxy-2-methyl-4-oxo-1,2,3,4-tetrahydroquinoline-1-carboxylate and ethyl 6-isopropoxy-7-methoxy-2-methyl-4-oxo-1,2,3,4-tetrahydroquinoline-1-carboxylate.

The activity of compounds of this invention as a tranquilizing agent has been shown by testing their effectiveness in one or more of the following tests:

A. Conditioned Avoidance Behavior [Maffi, J. Pharmacol., 11, 129 (1959); Sidman, Science, 118, 157 (1953)].

B. Sedation Test — The subjects were male Sprague-Dawley rats weighing approximately 200 g and fed and watered ad lib before the experiment. Eight rats were assigned to each treatment group, and each rat was used only once.

1.5 hr. after oral treatment, each rat was placed in a standard jiggle cage for 1 hr. In this device, the subject was confined in a 6 × 6 × 3.5 in. Plexiglas enclosure. The enclosure was attached to one end of a flexible steel arm. This configuration, all of which was housed in a soundproof, ventilated chamber, allowed the enclosure to jiggle slightly with any movement. A force displacement transducer mounted under the jiggle cage monitored any vertical movement of the subject. The output of the transducer was coupled to a strain-gauge amplifier and to an analog recorder. To provide digital data of movement/non-movement times a trigger circuit was constructed in which the output of the strain-gauge amplifier was attentuated and rectified to activate a relay whenever the subject moved. When the relay remained deenergized for 3 sec., a timer was activated. Movement by the subject energized the relay and stopped the timer until 3 sec. of immobility recurred. This 3 sec. criterion eliminated brief periods of inactivity observed even in active rats.

The threshold level was made sensitive enough to activate after small movements, but not after respiratory movements in an anethesized subject. A force displacement equal to a weight change of between 5 and 10 g. was found to be a good threshold level for 200 rats.

C. Symtomatology — Four groups of 3 mice were treated intraperitoneally with 31.6, 100, 316, or 1000 mg/kg of the test compound. At ½, 2, or 5 hours after treatment, symtomatological observations were made; observations were all-or-none, and classified into autonomic, muscular, reflex or behavioral categories. When pronounced symptoms occurred at 31.6 mg/kg further dose reductions by $1\log_{10}$ 0.5 units were made. Symptoms interpreted as indicating tranquilizer activity included decreased spontaneous motor activity, inability to ride a rotating rod (rotorod), and inability to remain on an inclined plane.

EXAMPLE 25

The following summarizes the tranquilizing activities of the compounds of this invention based on the above-described tests.

The activity of compounds of this invention as an analgesic agent has been shown by testing their effectiveness in one or more of the following tests:

D. Suppression of the "jump" component of the Flinch-Jump Test [Evans, Psychopharmacologia, 2, 318 (1961)].

E. Escape Titration Test [Weiss et al, Science, 128, 1575 (1958)].

F. Suppression of Writhing Test [Siegmund et al, Proc. Sec. Exp. Biol., 95, 729 (1957)].

G. Hot Plate Test [Eddy et al, J. Pharm. Exp. Ther., 107, 385 (1953)].

H. Tail Flick Test [Witkin et al, Proc. Soc. Exp. Biol., 101, 377 (1959)].

EXAMPLE 26

The following summarizes the analgesic activities of compounds of this invention based on the above-described tests.

| Structure | Conditioned Avoidance Behavior | | Sedation Test | Symptomatology |
|---|---|---|---|---|
| | Maffi | Sidman | | |
| 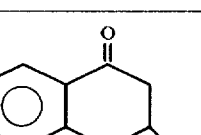 | 0.5 hr.: Active at 56, 32 and 10 mpk | Active in 3 of 3 animals at 32 mpk; 2 of 3 animals at 17.8 mpk | Active at 32 mpk Inactive at 10 mpk | Rotorod: 3.2–10 mpk Inclined Plane: 32–100 mpk |
| 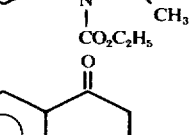 | | | | Rotorod: 100–316 Inclined Plane: 100–316 |
| 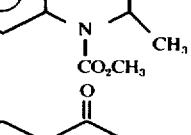 | | | | Rotorod: 32–100 Inclined Plane: 100–316 |
| 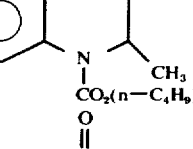 | | | | Rotorod: 100–316 mpk Inclined plane: 100–316 mpk |

| Structure | Rat Flinch Jump Test Jump Threshold (i.p.) | | | | | Escape Titration | PBQ Writhing | Hot Plate % Protected 100 mpk | | Tail Flick % Protected 100 mpk | | $LD_{50}$ (mpk) |
|---|---|---|---|---|---|---|---|---|---|---|---|---|
| | 32 mpk | | 10 mpk | | 3.2 mpk | | | | | | | |
| | .5 h | 2 h | .5 h | 2 h | .5 h | 2 h | | | .5 h | 2 h | .5 h | 2 h | |
| 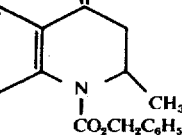 | >2.2 | >2.2 | Run one: >2.2  1.6 Run two: 2.2  .8 | | .8 | .6 | Active at 32 mpk (p.o.) | Inactive at 100 mpk | 0 | 0 | 0 | 0 | >1000 |

-continued

| Structure | Rat Flinch Jump Test Jump Threshold (i.p.) | | | | | | PBQ Writhing | Hot Plate % Protected 100 mpk | | Tail Flick % Protected 100 mpk | | LD$_{50}$ (mpk) |
|---|---|---|---|---|---|---|---|---|---|---|---|---|
| | 32 mpk | | 10 mpk | | 3.2 mpk | | Escape Titration | | | | | |
| | .5 h | 2 h | .5 h | 2 h | .5 h | 2 h | | | .5 h | 2 h | .5 h | 2 h | |
| 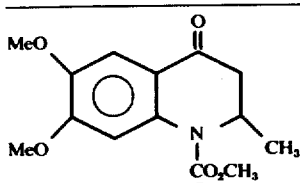 | 1.6 | 1.2 | | | | | | Inactive at 100 mpk | 0 | 0 | 0 | 0 | >1000 |
| 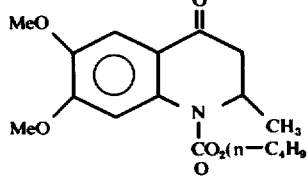 | 1.6 | 1.2 | | | | | | Inactive at 100 mpk | 0 | 0 | 0 | 0 | 316–1000 |
| 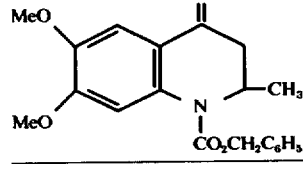 | | | | | | | | Inactive at 100 mpk | | | | | >1000 |

The following results were obtained when the performance of the d-, l and dl- forms of a compound of the invention were compared in the Rat Flinch Jump Thresholds The control Jump Threshold using saline were 0.78 at 0.5 hr. and 0.92 at 2 hr.

| | Jump Threshold | | | | | |
|---|---|---|---|---|---|---|
| | 56 mpk | | 32 mpk | | 17.5 mpk | |
| Compound | .5 hr | 2 hr | .5 hr | 2 hr | .5 hr | 2 hr |
| d-ethyl 6,7-dimethoxy-2-methyl-4-oxo-1,2,3,4-tetrahydroquinoline-1-carboxylate | 1.51 | 1.45 | 1.45 | 1.38 | 1.26 | 0.98 |
| l-ethyl 6,7-dimethoxy-2-methyl-4-oxo-1,2,3,4-tetrahydroquinoline-1-carboxylate | 1.05 | 0.86 | 0.85 | 0.86 | 0.92 | 0.92 |
| dl-ethyl 6,7-dimethoxy-2-methyl-4-oxo-1,2,3,4-tetrahydroquinoline-1-carboxylate | 1.58 | 1.45 | 1.38 | 1.18 | 1.26 | 0.98 |

The following results were obtained when 6,7-dimethoxy-2-methyl-4-oxo-1,2,3,4-tetrahydroquinoline, ethyl 6,7-dimethoxy-2-methyl-4-oxo-1,2,3,4-tetrahydroquinoline-1-carboxylate and benzyl 6,7-dimethoxy-2-methyl-4-oxo-1,2,3,4-tetrahydroquinoline-1-carboxylate were compared in the Rat Flinch Jump Test. The dosage of test compound was 56 mpk. Each of the compounds was in its racemic form.

| | Jump Threshold | |
|---|---|---|
| Compound | 0.5 hr. | 2.0 hr. |
| 6,7-dimethoxy-2-methyl-4-oxo-1,2,3,4-tetrahydroquinoline | 1.47 | 1.10 |
| ethyl 6,7-dimethoxy-2-methyl-4-oxo-1,2,3,4-tetrahydroquinoline-1-carboxylate | 1.58 | 1.42 |
| benzyl 6,7-dimethoxy-2-methyl-4-oxo-1,2,3,4-tetrahydroquinoline-1-carboxylate | 1.47 | 1.21 |

The activity of compounds of this invention as analgesic agents has also been shown by testing their effectiveness in a Mouse Tail Pinch Technique. This technique was a modification of the Haffner procedure [Deutsche Med. Wochenschrifte, 55, 731–732 (1929)] in which the mice were strongly pinched on the base of the tail. An audible squeak was elicited in normal non-drugged mice. Lack of an audible squeak was taken as indication of analgesic activity in drugged mice.

EXAMPLE 27

The following summarizes the analgesic activities of compounds of this invention based on the aforesaid Mouse Tail Pinch Technique.

| Structure | Mouse Tail Pinch $ED_{50}$ (mpk) |
|---|---|
| MeO, MeO — quinolinone — $CO_2C_2H_5$, $CH_3$ | >100 |
| MeO, MeO — quinolinone — $CO_2CH_3$, $CH_3$ | 100–316 |
| MeO, MeO — quinolinone — $CO_2(n-C_4H_9)$, $CH_3$ | >32 |

What is claimed is:

1. The racemic mixture of a compound of the formula

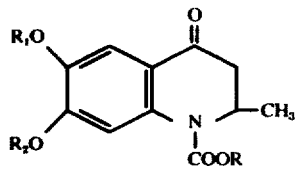

wherein R is selected from the group consisting of alkyl having from one to four carbon atoms and benzyl; and $R_1$ and $R_2$ are each alkyl having from one to four carbon atoms.

2. A racemic mixture according to claim 1, wherein $R_1$ and $R_2$ are each methyl.

3. The racemic mixture according to claim 2, wherein R is ethyl.

4. The racemic mixture according to claim 2, wherein R is benzyl.

5. The dextrorotatory enantiomer of a compound of the formula

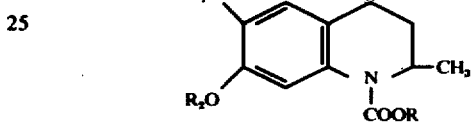

wherein R is selected from the group consisting of alkyl having from one to four carbon atoms and benzyl; and $R_1$ and $R_2$ are each alkyl having from one to four carbon atoms.

6. A dextrorotatory enantiomer according to claim 5, wherein $R_1$ and $R_2$ are each methyl.

7. The dextrorotatory enantiomer according to claim 6, wherein R is ethyl.

8. The dextrorotatory enantiomer according to claim 6, wherein R is benzyl.

* * * * *